(12) United States Patent
Chou et al.

(10) Patent No.: US 8,721,328 B2
(45) Date of Patent: May 13, 2014

(54) PATCH FOR ORAL HEALTH CARE

(71) Applicant: Toothfilm Biotech Innovation Co., Ltd., Taipei (TW)

(72) Inventors: Hsien-Sung Chou, Taipei (TW); Chen-Feng Ma, Taipei (TW); Guo-Ren Li, Taipei (TW)

(73) Assignee: Toothfilm Biotech Innovation Co., Ltd., Taipei (TW)

( * ) Notice: Subject to any disclaimer, the term of this patent is extended or adjusted under 35 U.S.C. 154(b) by 0 days.

(21) Appl. No.: 13/728,432

(22) Filed: Dec. 27, 2012

(65) Prior Publication Data

US 2014/0010851 A1    Jan. 9, 2014

(30) Foreign Application Priority Data

Jul. 3, 2012  (TW) .............................. 101123863 A (51) Int. Cl.
    *A61K 8/02*  (2006.01)
(52) U.S. Cl.
    USPC ............................................. 433/39; 424/435

(58) Field of Classification Search
    USPC .............................................. 433/37, 80, 215
    See application file for complete search history.

(56) References Cited

U.S. PATENT DOCUMENTS

| | | | |
|---|---|---|---|
| 6,551,579 B2 | 4/2003 | Sagel et al. | |
| 6,884,426 B2 | 4/2005 | Sagel et al. | |
| 2005/0175959 A1 | 8/2005 | Jodaikin et al. | |
| 2010/0028829 A1* | 2/2010 | Lewis et al. ..................... | 433/80 |

* cited by examiner

*Primary Examiner* — Walter Webb
(74) *Attorney, Agent, or Firm* — WPAT, P.C.; Anthony King (57) ABSTRACT

The present invention is directed to a U-shaped patch for oral health care, comprising a thin film layer and a support layer, and the inner and outer margin of the U-shaped patch have at least one notch or cut line so that the patch can be folded as a three-dimensional concave shape, wherein the thin film layer comprises a health care agent. The present invention uses a two-layered design comprising a thin film layer and a support layer, and a health care agent in the adhesive layer effective for caries prevention, whitening and/or remineralization. The patch of the present invention can closely cover teeth with the thin film layer to enable the health care agent to tightly contact the teeth so as to increase the efficacy on tooth care.

12 Claims, 6 Drawing Sheets

PATCH FOR ORAL HEALTH CARE

FIELD OF THE INVENTION

This invention relates to an oral care patch. Particularly the invention provides a U-shaped oral care patch.

BACKGROUND OF THE INVENTION

Rising levels of prosperity and quality of life have driven higher consumer expectations regarding quality of oral health and esthetic norms for tooth appearance. Many tooth tray or paste products for enhancing oral health and tooth whitening are commercially available to satisfy these expectations, both over-the-counter products (OTC products) and products requiring a dentist's prescription. While OTC products are inexpensive, they have known limitations. For example, since the OTC products adopt one-size, uniformly shaped trays, they do not fit various tooth sizes and shapes, and thus cause irritation to teeth due to poorly fitting trays and excessively applied gels.

On the other hand, products requiring prescription are manufactured according to the contour and size of the patient's teeth This solves the problems associated with OTC products to some extent, but prescription products are disadvantageously expensive and require regular dental visits. In addition, tooth whitening trays are thick, have poor adhesion and cause a foreign body sensation during application. As reusable products, they also require washing before and after use to prevent bacterial growth.

In order to solve the above-mentioned disadvantages of tooth trays, tooth whitening products in the form of pastes have been developed. However, most of the products developed thus far fail to effectively resolve the problem of poor adhesion and are not designed to completely cover the inner and outer sides of the teeth.

SUMMARY OF THE INVENTION

The invention provides a tooth tray patch for oral care to resolve the problem of poor adhesion, meet the requirement for completely covering inner and outer sides of teeth, provide a broader range of tooth care efficacy, such as anti-caries, and avoid health problems caused by reuse of tooth trays. The tooth tray patch for oral health care is designed to increase adhesion to teeth, completely cover the front and back of teeth, and provide care effects besides whitening, for example, anti-caries, wherein the front of teeth includes labial side and buccal side of both the upper and lower teeth, and the back of teeth includes lingual side and palatal side of the lower teeth and upper teeth. The patch of the present invention can be disposed after use to avoid the problem of bacteria growth resulting from reuse.

DETAILED DESCRIPTION OF THE INVENTION

In the specification and claims, the singular forms "a," "an," and "the" include the plural unless the context clearly dictates otherwise. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

In order to achieve the aforesaid purpose, the present invention provides a U-shaped oral care patch, comprising a thin film layer and a support layer, wherein one side of the thin film layer provides attachment to teeth and the other side of the thin film layer is attached to the supporting layer, and the inner and outer margins of the thin film layer and the supporting layer of the U-shaped patch have at least one notch or cut line so that the patch can be folded as a three-dimensional concave shape. In one embodiment, an oral care agent can be coated in the side of the thin film layer, which is opposite to the side of the thin film layer connected to the support layer.

The term "support layer" refers to a layer supporting the shape of the patch, and being easily removed from the thin film layer. In one embodiment of the present invention, the support layer provides protection for the patch. In another embodiment, the support layer is bonded to the surface of the thin film layer. Preferably, the support layer is selected from the group consisting of gelatin, aluminum foil, regenerated silk fiber, polyurethane (PU), polyethylene (PE), polypropylene (PP), polyesters, nylon, paper, polyethylene terephthalate (PET), polylactic acid (PLA), chitosan, cellulose acetate phthalate, polyvinyl acetate, ethyl cellulose, polymethylmethacrylate, methacryloyl ethyl betaine/acrylate copolymer, methacrylic acid copolymers, methacrylic acid aminoalkyl ester copolymer or a mixture thereof.

Preferably, the thin film layer is selected from the group consisting of polyurethane (PU), polyethylene (PE), polypropylene (PP), polyesters, nylon, polyvinyl alcohol (PVA), polylactic acid (PLA), chitosan, polyvinyl methyl ether/maleic acid copolymer (PVM/MA copolymer), polyethylene oxide/polypropylene oxide copolymer (PEO/PPO copolymer), polyvinylpyrrolidone-vinyl acetate copolymer (PVP/VA copolymer), polyethylene oxide (Polyox), polyvinylpyrrolidone (PVP), γ-polyglycolic acid (γ-PGA), polyquaternium, carboxypolymethylene, carboxymethyl cellulose (CMC), hydroxypropyl methylcellulose, hydroxyethylcellulose, hydroxypropylcellulose, gels, gelatin, alginate, regenerated silk fiber, or a mixture thereof. The thin film layer may be a scour-resistant water-soluble polymer, for example, CMC, to make the thin film layer scour resistant and prevent over-dilution of the health care agent. The thin film layer may be a water-soluble polymer for inhibiting microbial growth, for example, chitosan, to prevent bacteria, fungus and biofilm.

The thin film layer may further comprise a thermosensitive polymer. It is well-known that thermosensitive polymer undergoes a phase transition at a cloud point (CP). Below the CP, the polymer exists in a water soluble form. Once the polymer is heated above the CP, water would be expelled from the polymer chain, resulting in aggregation/precipitation of the polymer. A thermosensitive polymer with CP which is slightly below body temperature, for example, Poly (N-isopropylacrylamide), is widely used for the design of thermosensitive drug delivery systems such as hydrogels.

In the invention, the patch may further comprise a thermosensitive polymer in a thin film layer. When the thin film of the invention contacts teeth, the thermosensitive polymer enables the oral care agent to be released from the thin film layer. In addition to the advantage for drug release, the thin film layer of the thermosensitive polymer is produced with environmentally friendly solvent, water, instead of an organic solvent. In one embodiment of the present invention, the thermosensitive polymer may be Poloxamer. Poloxamer has good solubility and low viscosity at low temperature (especially less than 10° C.). The viscosity is maximum at about room temperature and drastically drops at around 55° C. Poloxamer provides excellent flow properties for storage at low temperature or processing at high temperature, and shows high viscosity when applied to the human body or used at room temperature, enabling it to effectively maintain the shape of the product or achieve the effect of drug release.

Preferably, the oral care agent is selected from the group consisting of a tooth whitening agent, an antibacterial agent, an antisensitive agent, an anti-caries agent, a remineralization agent, a sweetener or a mixture thereof. The sweetener includes but is not limited to peppermint, xylitol, etc.

In one embodiment, the support layer of the invention has a set of arcuate fold lines designed to match the dentition. More preferably, the set of arcuate fold lines comprises a front fold line and a back fold line, the front fold line and the back fold line are close to or overlap with each other at the central portion of the patch, the distance between the front fold line and the back fold line at the central portion of the patch is larger than that at the end portion of the patch.

Figure 9:
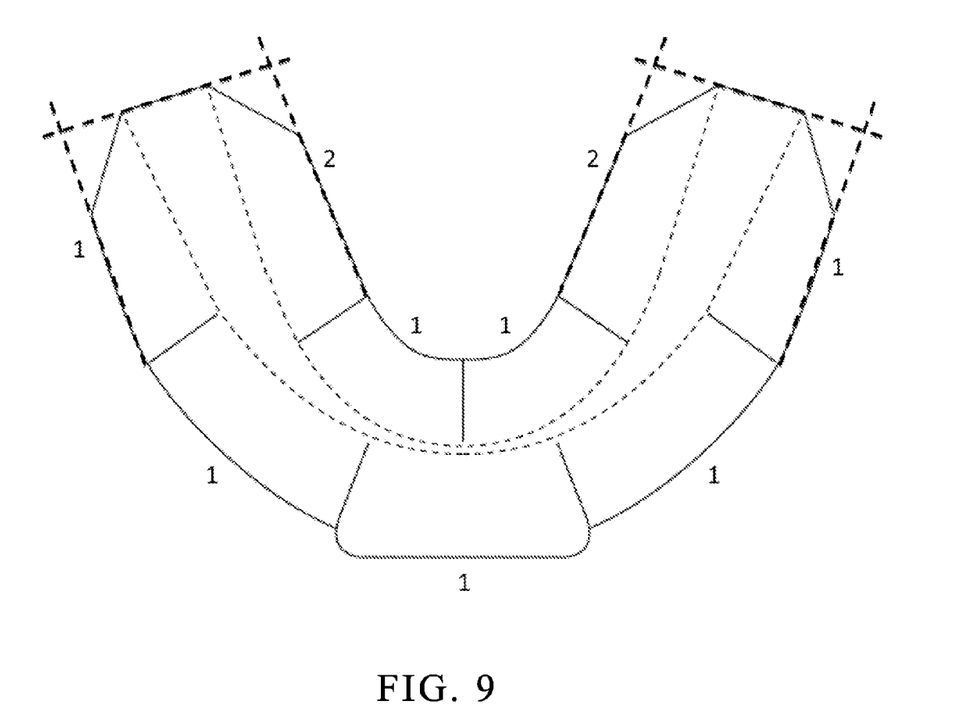
FIG. 9 shows a developed view of another preferred embodiment of the present invention.

Preferably, the patch of the invention has a plurality of notches or cut lines in the thin layer and the supporting layer. More preferably, the inner margin of the U-shaped patch has an odd number of notches or cut lines, and the outer margin of the U-shaped patch has an even number notches or cut lines. In one embodiment of the present invention, the inner margin of the U-shaped patch has three or five notches or cut lines, and the outer margin of the U-shaped patch has four or six notches or cut lines. Preferably, as shown in FIG. 9, the inner margin of the U-shaped patch is divided by three cut lines into four parts, the ratio of which is about 2:1:1:2, and the outer margin of the U-shaped patch is divided by 4 cut lines into 5 parts, the ratio of which is about 1:1:1:1:1.

Preferably, the notch or cut line is set on the inner and outer margins of the U-shaped patch, according to an interdental gap. Preferably, the notch or cut line extends to the front fold line and the back fold line from the inner or outer margin of the U-shaped patch.

In one embodiment, the patch of the invention comprises a protection layer attached to the thin film layer. The term "protection layer" provides the same function as that of the "support layer and can replace the supporting layer." More preferably, the protection layer is paper. The protection layer is removed before the patch for oral care is affixed to the teeth.

Preferably, the protection layer has the same front fold line, back fold line and notch or cut line as the patch.

Preferably, the patch of the invention is bent along the front fold line and the back fold line to form an arcuate three-dimensional concave article.

In the present invention, the method for setting an oral care agent in the thin film layer includes but is not limited to: impregnating the thin film layer in a container filled with a health care agent, or coating a oral care agent onto the thin film layer by the scraper, to combine the oral care agent with the thin film layer and then set the oral care agent in the thin film layer.

In the present invention, chitosan has but is not limited to a molecular weight of from 5 thousand Da to 2 million Da.

In the present invention, material of the aforesaid thin film layer includes but is not limited to woven fabrics, non-woven fabrics, or any fabric materials having regular or irregular net structure resulted from weaving techniques. The aforesaid fabrics have certain thickness and flexibility.

In the present invention, the aforesaid front fold line and back fold line include but are not limited to a pressure mark of the U-shaped patch for oral health care formed by compression molding or a line printed on the support layer and optionally the thin film layer.

In the present invention, the aforesaid anti-caries agent includes but not limited to a fluoro-containing compound. The fluoro-containing compound includes but not limited to sodium fluoride, tin fluoride, sodium monofluorophosphate, or a mixture thereof.

In the present invention, the aforesaid tooth whitening agent or bleaching agent includes but is not limited to a peroxide, a percarbonate, a peroxyacid, a whitening active agent or a mixture thereof.

In the present invention, the aforesaid peroxide includes but is not limited to hydrogen peroxide, calcium peroxide or carbamide peroxide.

In the present invention, the aforesaid whitening active agent includes but is not limited to a hypochlorite for enhancing whitening effect.

In the present invention, the aforesaid remineralization agent includes but is not limited to calcium phosphates, wherein the source of calcium and phosphate is selected from the group consisting of anhydrous dicalcium phosphate, tetracalcium phosphate, dicalcium phosphate dihydrate, tricalcium phosphate and a mixture thereof.

In the present invention, the aforesaid remineralization agent includes but is not limited to calcium salts, wherein the calcium salt is calcium fluoride, calcium sulfate, calcium ascorbate, calcium oxide, calcium hydroxide, calcium lactate, calcium citrate, calcium gluconate, or a mixture thereof.

The present invention also provides a method for improving oral health, including:

a) providing a U-shaped patch for oral care, comprising a thin film layer and a support layer, wherein the inner and outer margins of the U-shaped patch have at least one notch or cut line, and the thin film layer comprises a health care agent, b) folding the patch, preferably along fold lines set on the support layer, to form an arcuate three-dimensional concave article, c) affixing the folded patch to teeth, and d) removing the support layer from the patch.

The present invention is characterized by combining a U-shaped patch for oral care with a two-layered design comprising a thin film layer and a support layer, and a health care agent in the thin film layer for caries prevention, whitening and/or remineralization. The patch of the present invention can completely and closely cover teeth with the thin film layer to enable the health care agent to tightly contact the teeth so as to increase the effect on tooth care. The patch of the present invention can be disposed after use to avoid the problem of bacteria growth resulting from reuse. In addition, the health care agent may be selected from an anti-caries agent, a whitening agent, and a remineralization agent, as needed.

Moreover, by the arcuate fold lines designed for different transverse planes of molar and incisor and the shape of arcus dentalis, the present invention allows a user to bend the patch of the present invention through a support layer, preferably along the front and back fold lines set on the support layer, to form an arcuate three-dimensional concave article matching the shape of the arcus dentalis of the user. In this way, the patch of the present invention can cover the entire dentition to closely and sufficiently contact the thin film layer of the present invention with the tooth face and increase the time of the reaction of the health care agent and the tooth face to improve care effect.

EXAMPLES

Figure 1:
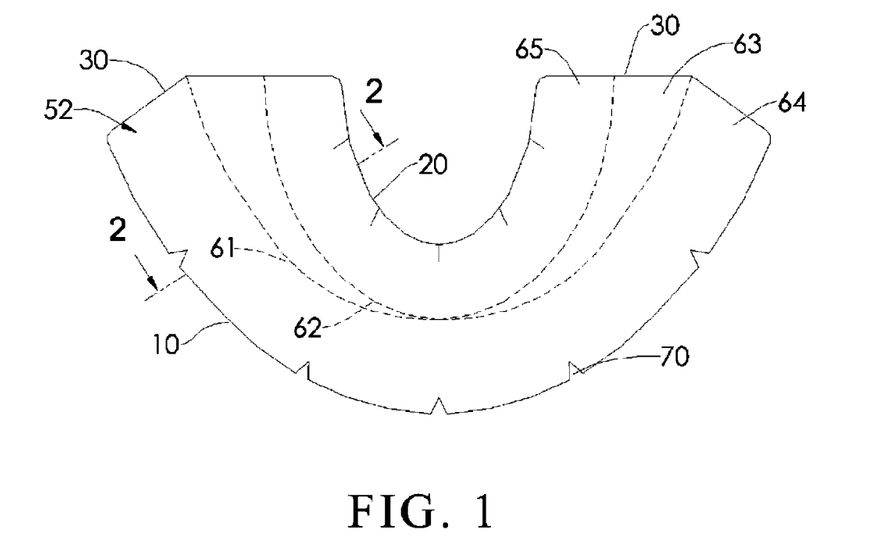
FIG. 1 shows a developed view of a preferred embodiment of the present invention.
Figure 2:
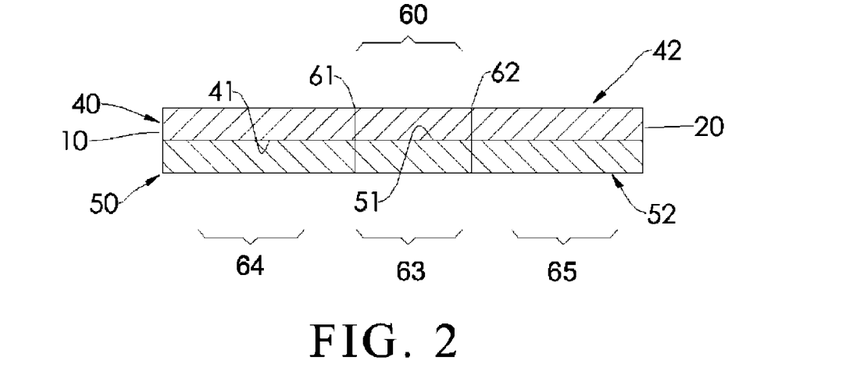
FIG. 2 shows a partial cross section of a preferred embodiment of the present invention.
Figure 3:
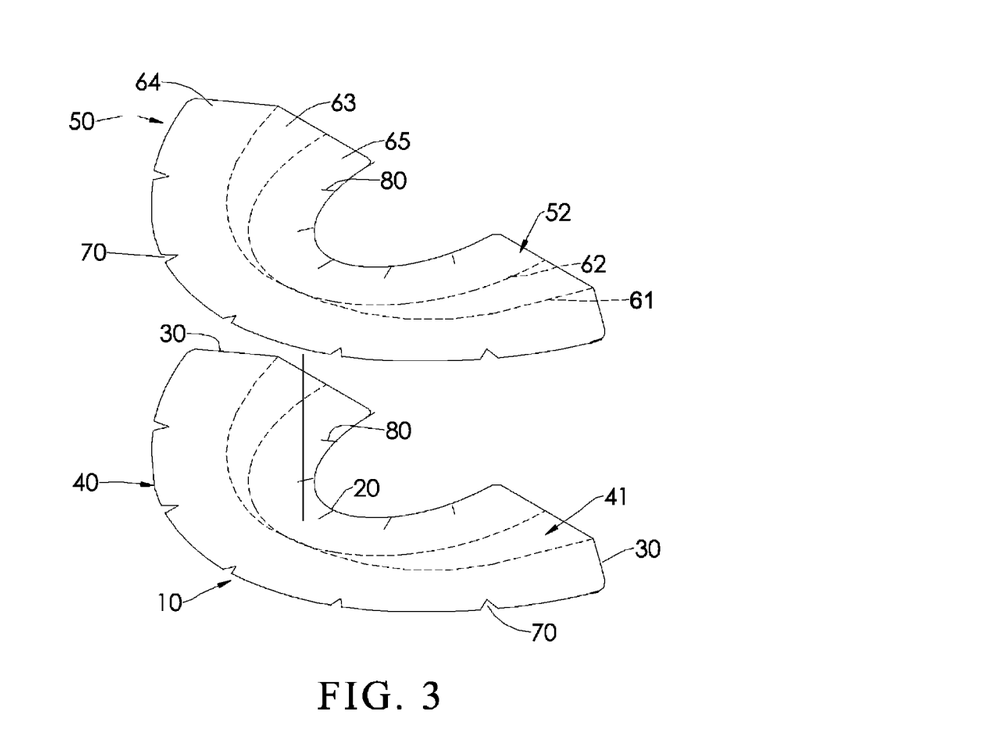
FIG. 3 is an exploded view of a preferred embodiment of the present invention.

Reference is made to FIG. 1 to FIG. 3. The U-shaped patch for oral care of the present invention has an outer margin 10, an inner margin 20, two side edges 30, a thin film layer 40, a support layer 50, a set of arcuate fold lines 60, a plurality of notches 70 and a plurality of cut lines 80.

The inner margin 20 is opposite to the outer margin 10. The outer margin 10 and the inner margin 20 are designed as an arc shape according to a dentition. The outer margin 10 has a smaller camber than the inner margin 20. The inner margin 20 defines a gap. The two side edges 30 are between the outer margin 10 and the inner margin 20.

The thin film layer 40 and the support layer 50 have a shape created by the outer margin 10, the inner margin 20 and the two side edges 30, and the support layer 50 is bonded to the thin film layer 40. The thin film layer 40 has an interface 41, an adhesive surface 42 and a health care agent. The adhesive surface 42 is opposite to the interface 41. A oral care agent, for example, chitosan, is set in the thin film layer 40. The support layer 50 has an interface 51 and an exposed surface 52. The interface 51 is bonded to the interface 41 of the thin film layer 40, and the exposed surface 52 is opposite the interface 51.

The set of arcuate fold lines 60 is located between the outer margin 10 and the inner margin 20 and extends from the adhesive surface 42 of the thin film layer 40 to the exposed surface 52 of the support layer 50. The set of arcuate fold lines 60 includes a front fold line 61 and a back fold line 62. The front fold line 61 is between the outer margin 10 and the back fold line 62. The front fold line 61 and the back fold line 62 are arc shaped. The camber of the front fold line 61 and the back fold line 62 correspond to the camber of the outer margin 10 and the inner margin 20. Therefore, the camber of the front fold line 61 is smaller than that of the back fold line 62. The central portion of the front fold line 61 overlaps with the central portion of the back fold line 62, and the distance between the front fold line 61 and the back fold line 62 gradually increases toward the end of each fold line, such that the distance defines a cross paste portion 63 which extends from the adhesive surface 42 of the thin film layer 40 to the exposed surface 52 of the support layer 50. The spacing between the front fold line 61 and the outer margin 10 defines a front paste portion 64, which extends from the adhesive surface 42 of the thin film layer 40 to the exposed surface 52 of the support layer 50. The spacing between the back fold line 62 and the inner margin 20 defines a back paste portion 65 which extends from adhesive surface 42 of the thin film layer 40 to the exposed surface 52 of the support layer 50.

The plural notches 70 link to the outer margin 10 to form the front paste portion 64. The plural notches 70 extend from the outer margin 10 in a direction toward the front fold line 61, wherein there is a set distance between every two adjacent notches 70.

The plural cut lines 80 link to the inner margin 20 to form the back paste portion 65. The plural cut lines 80 extend from the inner margin 20 in a direction toward the back fold line 62, wherein there is a distance between every two adjacent cut lines.

In one preferred embodiment of the present invention, the thin film layer 40 includes but is not limited to fabrics, which may be woven fabrics, non-woven fabrics, or any fabric materials having regular or irregular net structure resulting from weaving techniques. The fabrics have a certain thickness and flexibility.

In one preferred embodiment of the present invention, the support layer is selected from the group consisting of gelatin and paper.

In one preferred embodiment of the present invention, the oral care agent is selected from the group consisting of a tooth whitening agent, an antibacterial agent, an antisensitive agent, an anti-caries agent, a remineralization agent, chitosan, a sweetener or a mixture thereof.

In one preferred embodiment of the present invention, before the U-shaped patch is used for oral care, an oral care agent is coated onto the adhesive surface 42 of the thin film layer 40 and is combined with the adhesive surface 42 of the thin film layer 40 so as to set the health care agent in the thin film layer 40. In another embodiment of the present invention, before the U-shaped patch is used for oral care, the thin film layer 40 is placed in a container filled with chitosan having a molecular weight of from 5 thousand Da to 2 million Da, so as to allow the chitosan to diffuse from the adhesive surface 42 to the interface 41.

In one preferred embodiment of the present invention, the anti-caries agent includes but is not limited to a fluoro-containing compound.

In one preferred embodiment of the present invention, the fluoro-containing compound includes but is not limited to sodium fluoride, tin fluoride, sodium monofluorophosphate, or a mixture thereof.

In one preferred embodiment of the present invention, the tooth whitening agent or bleaching agent includes but is not limited to a peroxide, a percarbonate, a peroxyacid, a whitening active agent or a mixture thereof.

In one preferred embodiment of the present invention, the peroxide includes but is not limited to hydrogen peroxide, calcium peroxide or carbamide peroxide.

In one preferred embodiment of the present invention, the whitening active agent includes but is not limited to a hypochlorite for enhancing whitening effect.

In one preferred embodiment of the present invention, the remineralization agent includes but is not limited to calcium phosphates, wherein the source of calcium and phosphate is selected from the group consisting of anhydrous dicalcium phosphate, tetracalcium phosphate, dicalcium phosphate dihydrate, tricalcium phosphate and mixtures thereof.

In one preferred embodiment of the present invention, the remineralization agent includes but is not limited to calcium salts, wherein the calcium salt is calcium fluoride, calcium sulfate, calcium ascorbate, calcium oxide, calcium hydroxide, calcium lactate, calcium citrate, calcium gluconate, or a mixture thereof.

Figure 4:
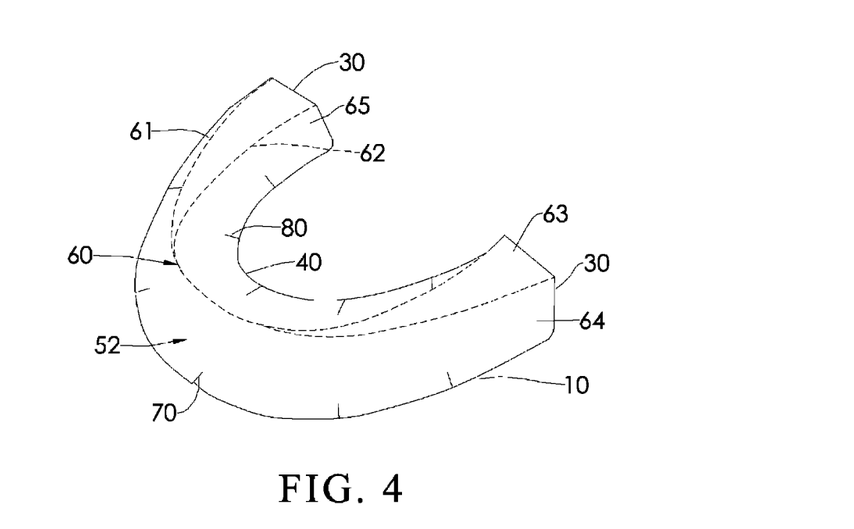
FIG. 4 shows a three-dimensional view of a preferred embodiment of the present invention when used for lower teeth.
Figure 5:
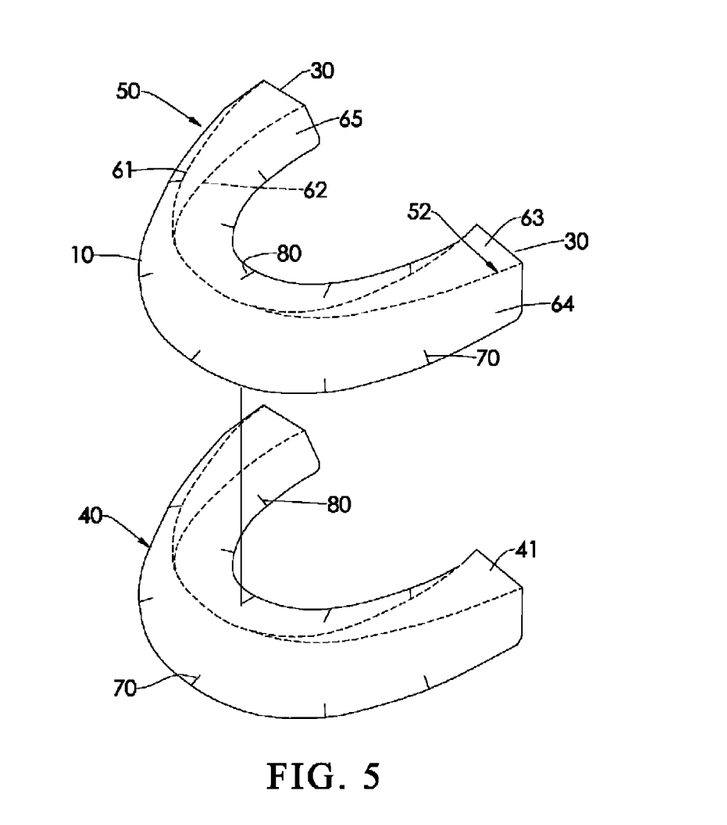
FIG. 5 is an exploded view of a preferred embodiment of the present invention.
Figure 6:
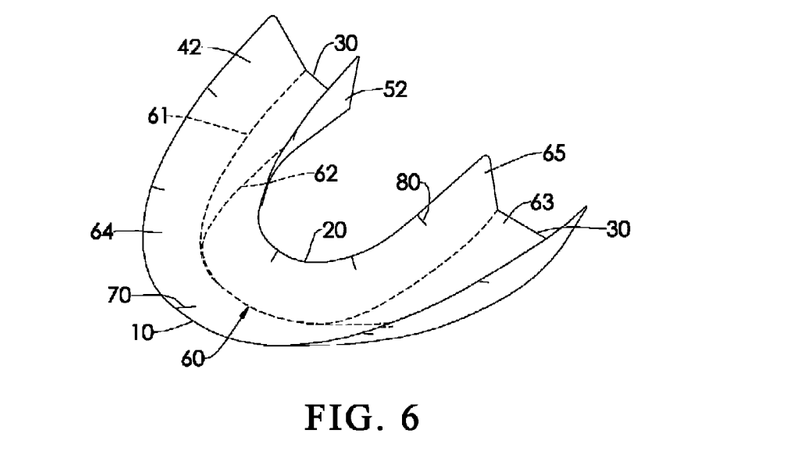
FIG. 6 shows a three-dimensional view of a preferred embodiment of the present invention when used for upper teeth.

Reference is made to FIG. 4 to FIG. 6. When using the U-shaped patch for oral care of the present invention, bending the patch results in an arcuate three-dimensional concave article matching the shape of a user's arcus dentalis. The bent patch for oral care, with the adhesive surface 42 of the thin film layer 40 facing toward the teeth and the exposed surface 52 of the support layer 50 facing away, is put on the upper or lower teeth to contact the adhesive layer 42 with the tooth surface and cover the entire teeth. In the meantime, the cross paste portion 63 adheres to the crown side of the molars and incisors, the front paste portion 64 adheres to the front tooth surface, and the back paste portion 65 adheres to the back tooth surface. By using a finger or tongue, the user may further make the front paste portion 64 more closely adhere to the front tooth surface through the notches 70 at the front paste portion 64, and make the back paste portion 65 more closely adhere to the back tooth surface through the cut lines 80 at the back paste portion 65. Moreover, the malleability of the support layer 50 of the outer layer allows the film for oral health care to adhere more closely to and be fixed on the teeth so as to enhance adhesion without adhering to skin or oral mucosa.

Figure 7:
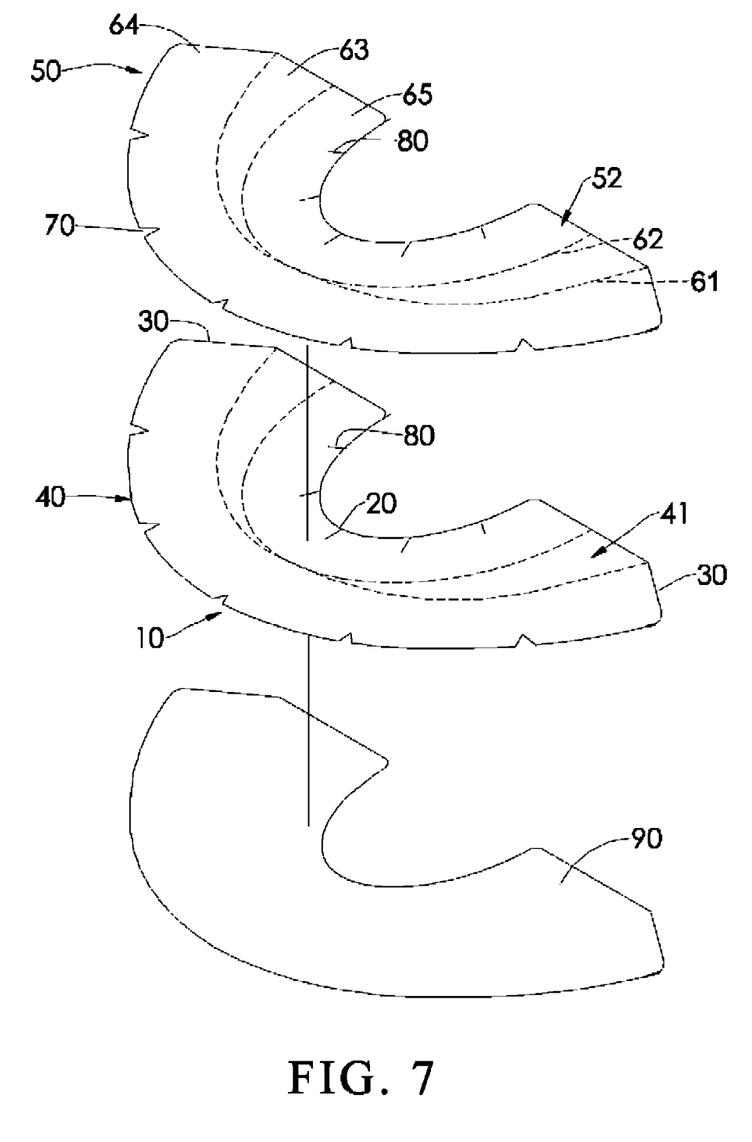
FIG. 7 is an exploded view of another preferred embodiment of the present invention.

Reference is made to FIG. 7. In another preferred embodiment of the present invention, the patch of the present invention further comprises a protection layer 90. The protection layer 90 adheres to the adhesive surface 42 of the thin film layer 40. The patch for oral care of the embodiment is different from the above-mentioned embodiment in that the protection layer 90 should be separated from the adhesive surface 42 of the thin film layer 40, followed by the above-mentioned procedures.

Figure 8:
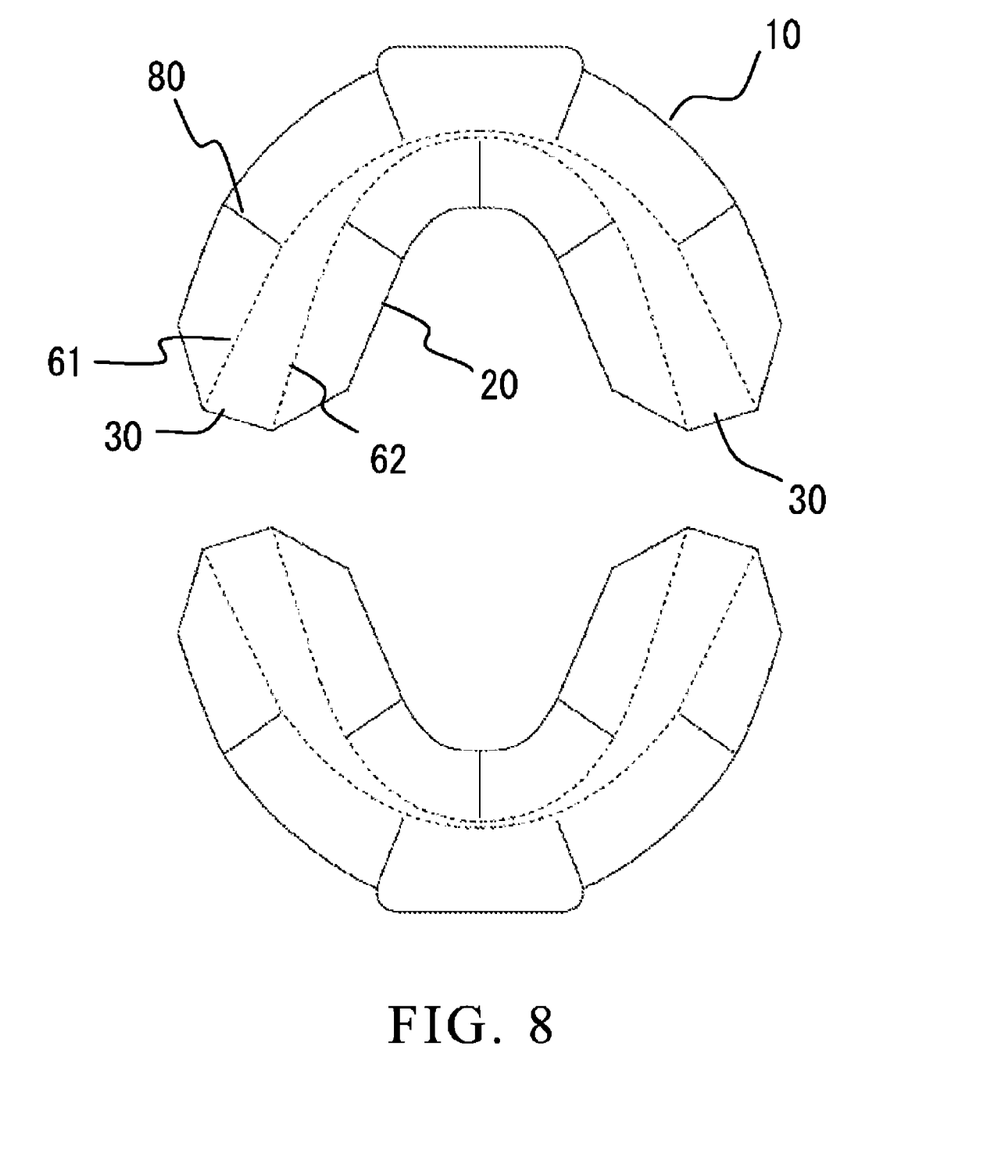
FIG. 8 shows a developed view of another preferred embodiment of the present invention.

Reference is made to FIG. 8. The U-shaped patch for oral care of the present invention has an outer margin 10, an inner margin 20, two side edges 30, a front fold line 61, a back fold line 62, four cut lines 80 in the outer margin 10 and three cut lines 80 in the inner margin 20.

The present invention is characterized by combination of a U-shaped patch for oral care having a two-layered design, comprising an thin film layer 40 and a malleable support layer 50, and a health care agent in the thin film layer 40 for caries prevention, whitening and/or remineralization. The malleable support layer 50 in the outer layer enables the patch of the present invention to closely cover teeth with the thin film layer 40, such that the oral care agent can tightly contact the teeth to increase the effect on tooth care. Moreover, by the set of arcuate fold lines 60 designed to accommodate the different transverse planes of the molars and incisors and the shape of arcus dentalis, the present invention allows users to bend the patch of the present invention along the front fold line 61 and the back fold line 62, to form an arcuate three-dimensional concave article matching the shape of the arcus dentalis, and the article includes front paste portion 64, back paste portion 65 and cross paste portion 63. In this manner, the patch of the present invention can cover the entire dentition to closely and sufficiently contact the thin film of the present invention with the tooth face and increase the time of the reaction of the oral care agent with the tooth face to increase the efficacy of care. Furthermore, the patch of the present invention can be disposed after use to avoid the problem of bacterial growth resulting from reuse. In addition, the oral care agent may be selected from an anti-caries agent, a whitening agent, and a remineralization agent, as needed, so as to provide a diverse range of tooth care effect.

Other embodiments of the invention will be apparent to those skilled in the art from consideration of the specification and practice of the invention disclosed herein. This application is intended to cover any variations, uses, or adaptations of the invention following the general principles thereof and including such departures from the present disclosure as come within known or customary practice in the art to which this invention pertains. It is intended that the specification and examples be considered as exemplary only, with the true scope and spirit of the invention being indicated by the following claims.

We claim:

1. A planar U-shaped oral care patch, comprising a thin film layer and a support layer, wherein one side of the thin film layer provides attachment to teeth and the other side of the thin film layer is attached to the supporting layer and the inner and outer margins of the thin film layer and the supporting layer of the planar U-shaped patch have at least one notch or cut line so that the planar U-shaped patch can be folded as a three-dimensional concave shape, wherein the entire planar U-shaped oral care patch is flat.

2. The planar U-shaped oral care patch of claim 1, wherein the support layer is selected from the group consisting of gelatin, aluminum foil, regenerated silk fiber, polyurethane (PU), polyethylene (PE), polypropylene (PP), polyesters, nylon, paper, polyethylene terephthalate (PET), polylactic acid (PLA), chitosan, cellulose acetate phthalate, polyvinyl acetate, ethyl cellulose, polymethylmethacrylate, methacryloyl ethyl betaine/acrylate copolymer, methacrylic acid copolymers, methacrylic acid aminoalkyl ester copolymer or mixtures thereof.

3. The planar U-shaped oral care patch of claim 1, wherein the thin film layer is selected from the group consisting of polyurethane (PU), polyethylene (PE), polypropylene (PP), polyesters, nylon, polyvinyl alcohol (PVA), polylactic acid (PLA), chitosan, polyvinyl methyl ether/maleic acid copolymer (PVM/MA copolymer), polyethylene oxide/polypropylene oxide copolymer (PEO/PPO copolymer), polyvinylpyrrolidone-vinyl acetate copolymer (PVP/VA copolymer), polyethylene oxide (Polyox), polyvinylpyrrolidone (PVP), γ-polyglycolic acid (γ-PGA), polyquaternium, carboxypolymethylene, hydroxypropyl methylcellulose, hydroxyethylcellulose, hydroxypropylcellulose, gels, gelatin, alginate, regenerated silk fiber, or mixtures thereof.

4. The planar U-shaped oral care patch of claim 1, wherein the thin film layer comprises a thermo-sensitive polymer.

5. The planar U-shaped oral care patch of claim 1, which further comprises an oral care agent selected from the group consisting of a tooth whitening agent, an antibacterial agent, antisensitive agent, an anti-caries agent, a remineralization agent, a sweetener or mixtures thereof.

6. The planar U-shaped oral care patch of claim 1, wherein the support layer has a set of arcuate fold lines for matching the dentition.

7. The planar U-shaped oral care patch of claim 6, wherein the set of arcuate fold lines comprises a front fold line and a back fold line, the front fold line and the back fold line are close to or overlap with each other at the central portion of the patch, and the distance between the front fold line and the back fold line at the central portion of the patch is less than that at the end portion of the patch.

8. The planar U-shaped oral care patch of claim 1, wherein the notch or cut line is set according to interdental gap.

9. The planar U-shaped oral care patch of claim 7, wherein the notch or cut line extends to the front fold line and the back fold line from the inner or outer margins of the patch.

10. The planar U-shaped oral care patch of claim 9, wherein the patch further comprises a protection layer attached to the thin film layer.

11. The planar U-shaped oral care patch of claim 1, wherein the inner margin is divided by three cut lines into four parts, the ratio of which is about 2:1:1:2, and the outer margin is divided by 4 cut lines into 5 parts, the ratio of which is about 1:1:1:1:1.

12. A method of using the planar U-shaped oral care patch of claim 1, comprising the steps of:
   a) providing the planar U-shaped oral care patch of claim 1,
   b) folding the planar patch as a three-dimensional concave shape,
   c) affixing the folded patch to teeth, and
   d) removing the support layer from the patch.

* * * * *